United States Patent [19]

McBride et al.

[11] Patent Number: 5,660,882

[45] Date of Patent: Aug. 26, 1997

[54] VACUUM ASSISTED APPLICATION OF THIN COATINGS ON APERTURED SUBSTRATES AND ARTICLES PRODUCED THEREFROM

[75] Inventors: Robert K. McBride, Jasonville; Carl D. Ray; Paul E. Thomas, both of Terre Haute, all of Ind.

[73] Assignee: Tredegar Industries, Inc., Richmond, Va.

[21] Appl. No.: 478,237

[22] Filed: Jun. 7, 1995

Related U.S. Application Data

[62] Division of Ser. No. 311,347, Sep. 23, 1994.

[51] Int. Cl.[6] ............... B05D 3/00; B05D 3/12; B05D 5/00
[52] U.S. Cl. ............... 427/294; 427/296; 427/420; 427/350
[58] Field of Search ............... 427/294, 296, 427/210, 420, 350; 604/365, 366, 378; 118/DIG. 4, 50, 407

[56] References Cited

U.S. PATENT DOCUMENTS

| | | |
|---|---|---|
| 2,186,957 | 1/1940 | Collings et al. . |
| 4,288,475 | 9/1981 | Meeker ............... 427/294 |
| 4,497,273 | 2/1985 | Mitter ............... 118/50 |
| 4,778,644 | 10/1988 | Cutto et al. ............... 264/557 |
| 4,806,411 | 2/1989 | Mattingly, III et al. ............... 428/139 |
| 4,839,076 | 6/1989 | Willman et al. ............... 252/90 |
| 4,839,216 | 6/1989 | Curro et al. . |
| 4,846,821 | 7/1989 | Lyons et al. ............... 604/369 |
| 4,995,930 | 2/1991 | Merz et al. ............... 156/209 |
| 5,158,819 | 10/1992 | Goodman et al. ............... 428/131 |
| 5,225,140 | 7/1993 | Hayashikoshi et al. ............... 264/571 |
| 5,281,208 | 1/1994 | Thompson et al. ............... 604/378 |
| 5,306,487 | 4/1994 | Karapasha et al. ............... 424/766 |
| 5,339,176 | 8/1994 | Buenger et al. ............... 604/367 |
| 5,368,910 | 11/1994 | Langdon . |
| 5,486,381 | 1/1996 | Cleveland et al. ............... 427/294 |

FOREIGN PATENT DOCUMENTS 4016348  11/1991  Germany .

*Primary Examiner*—Shrive Beck
*Assistant Examiner*—Fred J. Parker
*Attorney, Agent, or Firm*—Emch, Schaffer, Schaub & Porcello

[57] ABSTRACT

A process for the manufacture of apertured, three-dimensional substrates having an extrusion coating material thereon, the coated substrate and an apparatus for making the coated substrate are disclosed. Successive portions of a continuous sheet of the apertured substrate which has a top surface and a bottom surface are passed into contact with a continuous moving perforated member. The coating material is supplied onto the top surface of the continuous moving substrate. The bottom surface of the substrate is subjected to a vacuum. The vacuum causes the coating material to flow onto the top surface of the substrate material and in certain embodiments, at least partially into the apertures in the substrate. The vacuum is maintained for a period of time sufficient for the coating material to bond to the substrate. The coated portions of the substrate are continuously removed from the moving member.

10 Claims, 2 Drawing Sheets

VACUUM ASSISTED APPLICATION OF THIN COATINGS ON APERTURED SUBSTRATES AND ARTICLES PRODUCED THEREFROM

This is a divisional of copending application Ser. No. 08/311,347 filed on Sep. 23, 1994.

TECHNICAL FIELD

The present invention relates to the application of a coating material onto an apertured three-dimensional substrate utilizing a vacuum coating process. The present invention is also useful for applying thin layers of the coating to thin thermally sensitive apertured substrates. The present invention is especially useful in applying coating material to microapertured polymeric webs such as those webs disclosed in the Goodman, Jr. et al., U.S. Pat. No. 5,158,819.

Other readily envisioned uses for the present invention include applying a coating material onto any suitable apertured three-dimensional substrate which requires a fluid impervious layer such as backsheets in single use absorbent articles including catamenial pads, diapers, incontinent articles, surgical drapes and the like.

BACKGROUND OF THE INVENTION

An extrusion coating process generally includes an extruder slot (cast) die mounted in a position above a substrate to be coated. The substrate moves past the die. Gravity causes a molten stream of the extrusion coating material to fall onto the substrate. The thickness of the extrusion coating is controlled by the rate of output from the die and the rate of speed at which the substrate is moving beneath the die. The substrate can be moved beneath the stream of extrusion coating material flowing from the die in various ways. In certain methods the substrate material is moved on a conveyor belt beneath the die. Other means include grabbing the substrate material and moving it on driven rollers, beds or the like. Still other coating methods involve transporting the substrate over a roller or through a set of nip rollers adjacent the slot die. The coating material extrudes from the slot die onto the substrate at the nip. The nip rolls add pressure to the substrate and coating material at the interface to aid in achieving a bonding between the coating material and the substrate.

These extrusion methods require that the coatings have a sufficient thickness such that the coating material completely coats the substrate and that there are no spaces or gaps in the coating material.

While it would be desirable to apply an extrusion coating to such type of film, various difficulties occur when using the currently known coating technologies. Until the present invention, both the thermal energy of the extrusion coating systems and the compressive energy of the nip roll systems made it virtually impossible to achieve good bonding between the apertured substrate and any coating material applied thereto without causing damage to the apertures or the substrate itself. This is of particular concern when a thin coating is desired to be applied to the substrate.

Previously, attempts to apply a coating material onto thin apertured three-dimensional materials which are particularly sensitive to excessive thermal loads have not met with success. The apertured three-dimensional material does not have sufficient mass to resist distortion under the required thermal load necessary to achieve a good bond between the extrusion coating material and the three-dimensional material.

It is therefore an object of the present invention to provide an improved method for applying a layer of coating material to apertured, three-dimensional thermally sensitive substrates.

It is still another object of the present invention to provide a fluid impervious article comprising an extrusion coating material bonded to a thermally sensitive polymeric layer having multiple apertures.

It is still another object of the present invention to provide a substantially fluid impervious article suitable for use as a backsheet for a disposable absorbent and used article such as diapers, catamenial pads, surgical dressings and the like.

DISCLOSURE OF THE INVENTION

One aspect of the present invention relates to a method for coating an apertured, three-dimensional substrate material. According to the present invention, a coating material is extruded onto a top surface of an apertured substrate. A vacuum is applied to a bottom surface of the substrate as the coating material flows onto the substrate. The vacuum pulls fluid through the apertures in the substrate. The vacuum pulls the coating material against the substrate. The coated substrate is held under the vacuum pressure for a sufficient time to allow the coating material to bond to the surface. In preferred embodiments, the substrate can be a microapertured material. A much thinner layer of coating material can be applied to the substrate than was previously thought possible. The coating material and the substrate achieve good bond strength through both adhesive bonding and mechanical bonding.

In one preferred embodiment, a thermally sensitive apertured substrate can be coated with a thin layer of coating material such that there is good bond strength between the substrate and the coating material without causing thermal distortion or damage to the substrate.

In a particularly preferred embodiment, the present invention comprises a composite backsheet having an outermost three-dimensional film layer having multiple apertures which face outwardly and which come into contact with a wearer or user's skin. The composite backsheet further has an inner layer comprised of a substantially liquid impervious extrusion coating material which prevents any material from penetrating or leaking through the liquid impervious coating material. The inner coating material layer is extruded onto the outer three-dimensional film layer using the method of the present invention.

Thus, composite articles of the present invention provide highly desirable liquid impervious pervious characteristics and also provide the advantage of the desirable tactile suede or cloth-like properties of the microapertured structures. The composite articles produced using the method and coated structure of the present invention exhibit lower levels of noise when subjected to movement relative to a wearer's body. Further, a composite article is sufficiently thin, soft and compliant and exhibits an attractive cloth-like tactile impression. The present invention thus relates a method for applying a thin layer of coating material onto delicate three-dimensional substrates at high speeds and at low costs and to the coated substrates formed thereby.

BEST MODE OF CARRYING OUT INVENTION

Figure 1:
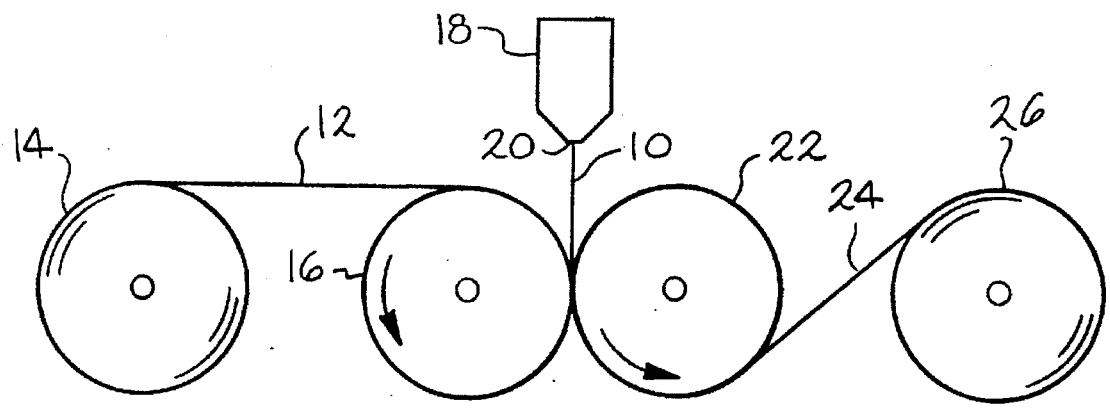
FIG. 1 is a simplified cross-sectional schematic illustration of a prior art process for extrusion coating a material onto a substrate.

According to one aspect of the present invention, in order to have an extruded coating material adhere or bond to a substrate, the coating material is supplied at a sufficiently elevated temperature at a point of interface. The interface is the point at which the two materials (the substrate and the coating) come into contact with each other. The temperature of the coating material is sufficiently elevated so that there is sufficient thermal energy supplied at the point of interface. The elevated temperature causes at least one of the following: melting and fusing of both the coating material and the substrate together to form a bond, a chemical reaction of one with the other to form a bond, or melting of the coating material on top of the substrate to form a cohesive bond.

In situations where the substrate does not melt and fuse with the coating material, the presence of thermal energy at the interface is no less important. In certain embodiments, the coating materials are designed to adhere to the substrates and are "thermally activated"; that is, no binding will occur until the coating material has achieved a sufficiently elevated temperature. It is also desired that the coating material substantially cover the top surface of the substrate including the apertures in the substrate. It is desired that a maximum amount of surface area of the coating material is brought into contact with the substrate. The maximum amount of surface contact helps form the bonding between the coating material and the substrate. It is to be understood that the cohesive bonding which occurs can be analogized to the phenomenon where a drop of oil is placed between two glass plates. When these plates are pressed together, the microscopic voids in the glass plates are filled by the oil and a form of suction exists. When one glass plate is lifted the other glass plate, which is cohesively bonded to the first glass plate, stays attached thereto.

It is important to understand that since the viscosity of fluids correlates to the temperature of the fluids, the higher the temperature, the less viscous the fluid. Therefore, maintaining a high temperature (i.e., low viscosity) as the coating material contacts the substrate is desired. This maintenance of thermal energy as, and after, the coating material contacts the substrate is controlled by two parameters of thermal dynamics, i.e., temperature and mass. The coating material is supplied at a sufficiently elevated temperature and at a sufficient mass in order to achieve a good bond. The substrate with the coating applied thereto is maintained at that sufficiently elevated temperature for a sufficient time for the bond to form.

Polymers, and in particular polymers designed for use as coating materials, have well-defined upper limits of temperature which can be manipulated before degradation of the polymer occurs. The well-defined thermal degradation limit of the polymer necessarily controls the amount of heat supplied to the extrusion coating process. The remaining parameter which can be controlled is the mass of the coating material applied to the substrate. The mass is controlled by regulating the thickness of the coating material being applied to the substrate. In many extrusion applications, it is desired to apply as thin a layer of coating material as possible to the substrate. However, if too thin a coating layer is applied, the coating layer quickly loses heat and cools too quickly. Without sufficient heat, the low mass of coating material does not bond to the substrate. Therefore, the parameters of mass, temperature of the coating material and the length of time at which the coating material and substrates are maintained at the proper temperature are controlled.

The thermal requirements of the extrusion coating process are further affected if the substrate itself is a thermally sensitive material. The amount of thermal energy applied to the thermally sensitive substrate by the coating material is necessarily limited by the amount of thermal energy the substrate can tolerate without being damaged. This is especially true for a three-dimensional polymeric film having microscopic apertures. The microscopic apertures have ends which are spaced apart from the plane of the film and the thickness of the film at these open ends thereof is further reduced. The resulting film material has a cloth-like or silky tactile effect which is desired in many film applications. However, these microscopic open ends are especially sensitive to temperature and have the lowest mass point of the polymeric film and, as such, are the most critical to protect.

One concern is how to protect the apertures when an absorbent core and/or backsheet is applied thereto. It is important that the apertures not be crushed during application of the core and/or backsheet. It is also important that the temperature and/or pressure applied during the application process not cause the ends of the apertures to melt and deform. When the apertures are melted or deformed, there is a less cloth-like tactile feeling to the coated film.

Referring now to FIG. 1, a prior art method of applying a coating material 10 to a substrate 12 is generally shown. In the prior art embodiment shown, the substrate 12 is unwound from a roll 14 and passed over a roller 16. A nip roll 22 is present adjacent the roller 16. A slot die 18 dispenses coating material 10 from an opening 20. Thereafter, a composite 24 which comprises the substrate 12 with the coating 10 adhered thereto can be wound up into a roll 26. In the extrusion process shown in FIG. 1, the coating material 10 is dispensed at a distance of approximately 1 to 3 feet above the nip defined by the roller 16 and the nip roll 22. Various problems with necking and beading of the coating material 10 occur at the nip as the coating material 10 is applied to a substrate 12. Therefore, the rate of speed at which the rollers 16 and 22 rotate is a limiting factor in applying an extrusion coating to a substrate 12. In addition, the coating material 10 generally must be delivered at a high temperature, generally about 550°–600° F., in order to have an adequate bonding between the substrate 12 and coating material 10. The coating only can be applied at thicknesses of about 0.5 mil and greater. This thickness or mass of the coating material is necessary in order to have sufficient heat transferred for a sufficient length of time in order to have bonding of the coating material to the substrate. Further, the nip pressure is needed to help bond the coating material to the surface.

Figure 2:
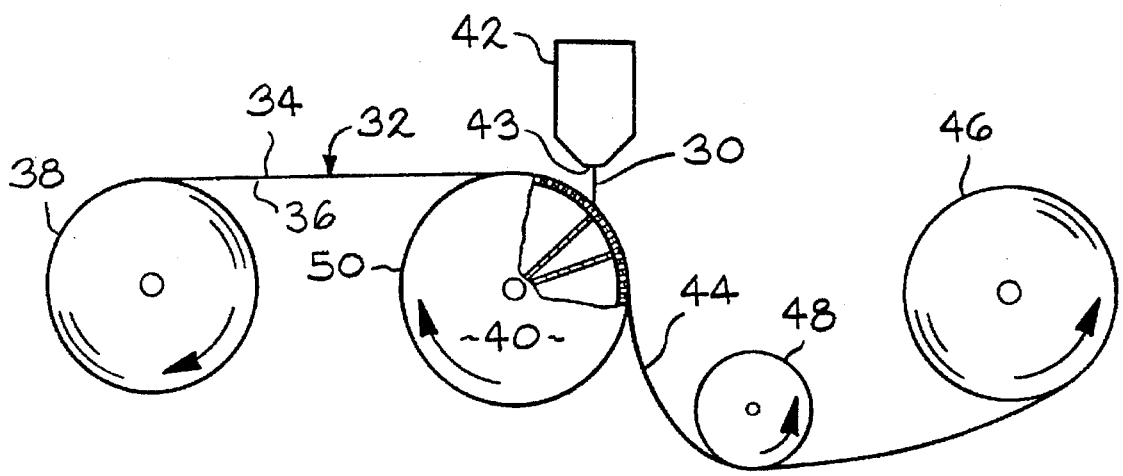
FIG. 2 is a simplified cross-sectional schematic illustration of a process for extrusion coating a material onto a substrate.
Figure 3:
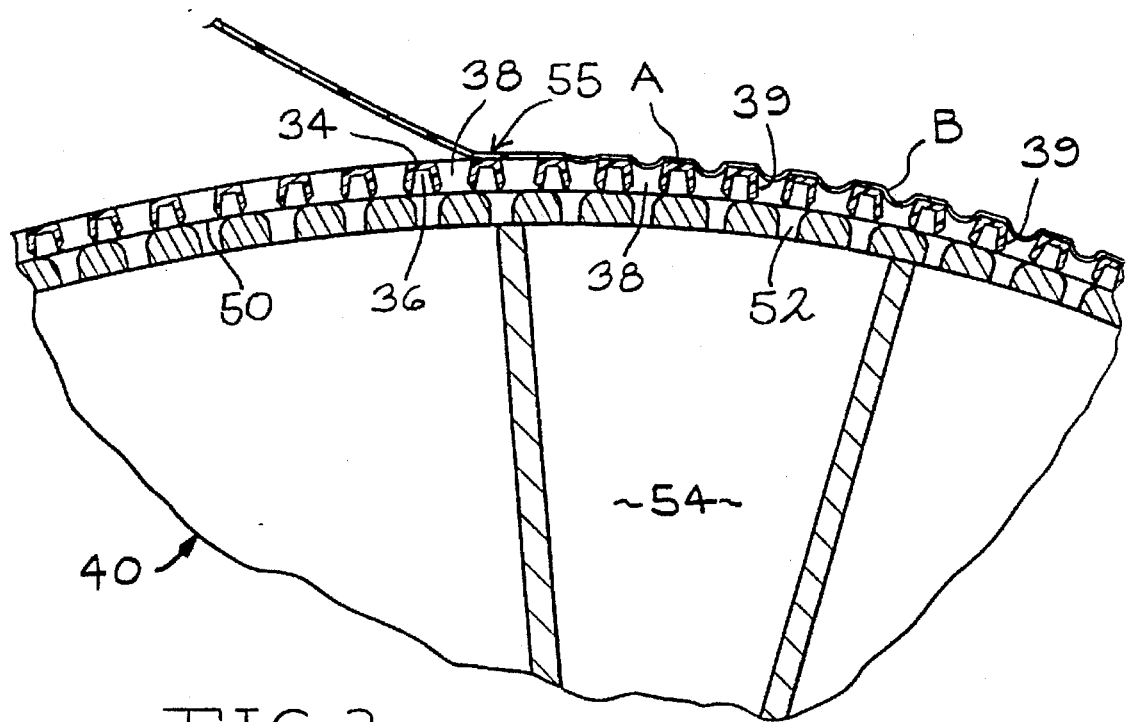
FIG. 3 is a simplified cross-sectional schematic illustration of a coating material being extruded onto a microapertured substrate.

The method of the present invention is generally shown in FIGS. 2 and 3. A coating material 30 is applied to an apertured substrate 32 having a top planar surface 34 and a three-dimensional or bottom surface 36 and a plurality of apertures 38 defined by sidewalls 39. In the embodiment shown the apertured substrate 32 is generally dispensed from a roll 37; however, it should be understood that the substrate 32 can be supplied by other means (not shown), including a film forming process. The apertured substrate 32 passes over a substrate moving member or drum 40. It is to be understood that the moving member 40 can be a conveyor belt-type apparatus or other moving member 40, such as a drum. For ease of illustration, the substrate moving member 40 is depicted herein as a drum.

The coating material 30 is dispensed from a slot die 42 having an opening 43. In preferred embodiments of the present invention, the opening 43 is less than about 1 foot from the drum 40. In especially preferred embodiments, the opening 43 can be approximately 2 to about 5 inches, or more preferably approximately 2–3 inches from the top surface 34 of the substrate 32 as it passes over the drum 40. The coating material 30 is dispensed onto the substrate 32 to form a composite material 44 which is then wound on a roll 46. In certain embodiments, it is contemplated that at least one other roller 48 such as an idler roller and/or cooling roll can be utilized with the present invention.

Referring now to FIG. 3 in particular, the drum 40 has a surface 50 which is highly perforated with a plurality of perforations 52 extending therethrough to allow a fluid such as air to pass through the perforations 52 in the surface 50 of the drum 40. When the moving member 40 is a drum, as shown in the figures herein, it is preferred that the surface 50 rotate at substantially the same rate of speed as the drum 40. A vacuum chamber 54, preferably located within the drum 40, is utilized to create a vacuum pressure between the top surface 34 and the bottom surface 36 of the substrate 32. As the coating material 30 is applied to the substrate 32, the vacuum causes the coating material 30 to be pulled against the top surface 34 of the substrate 32 and partially into the apertures 38 of the substrate 32. The vacuum is sufficient to pull the coating material 30 against the top surface 34 of the substrate 32 while maintaining the integrity of the coating material 30. In preferred embodiments, the coating material 30 is applied to the top surface 34 of the substrate 30 at an interface point 55 just prior to applying the vacuum to the substrate 30.

The vacuum pulls fluid, preferably air, which is present in the apertures 38 from the top surface 34 to the bottom surface 36 of the substrate 32. When the coating material 30 is applied to the substrate 32, the coating material 30 forms a barrier between the atmospheric pressure which would otherwise displace the air evacuated by the vacuum in the substrate 32. The removal of air from the apertures 38 causes the coating material 30 to be pulled against the top surface 34. The vacuum is applied such that sufficient pressure pulls the coating material 30 without perforating or tearing holes in the coating material 30.

The bond strength between the coating material 30 and the substrate 32 can be controlled by adjusting the vacuum pressure applied to the lower surface 36 of the substrate 32. A stronger vacuum pulls more coating material 30 into the apertures 38 and creates a stronger bond.

In the embodiment shown, the coating material 30 is initially formed by extrusion of a resin melt, such as polyethylene. It is also within the contemplated scope of the present invention that the coating material can be any suitable polymeric material which is applied to the apertured substrate at an elevated temperature, such that the coating material substantially conforms to the top surface of the apertured substrate. Thus, while not shown in the figures herein, it is to be understood that the coating material can be supplied as a polymeric web or film which is heated to an elevated temperature, so as to cause the polymeric coated material to melt, chemically bond or fuse onto the substrate and then solidify on the substrate.

According to the present invention, by varying the rate of speed of rotation of the drum as it moves the substrate, the amount of vacuum pressure applied to the substrate, and the rate of application of the coating material, it is now possible to apply a thin layer of coating material to an apertured substrate.

The coated substrate composite 44 is often subjected during use to peeling or shear forces. The bond strength between the coating material 30 and the substrate 32 is a key factor in determining whether composite 44 will remain intact and not peel apart. The peeling forces are typically applied in a normal (90°) angle to any surface of the composite 44. According to the method of the present invention, the coating material 30 is pulled into the apertures 38 and partially coats the sidewalls 39 defining each aperture 38. The mechanical strength required to force the coating material 30 into apertures 38 provides an additional force (mechanical) which is beyond the thermal and adhesive forces already present between the substrate 32 and the coating material 30. Thus, if the adhesive force is in itself inadequate to provide the required bond strength, the additional mechanical force present in the composite 44 provides the additional bond strength to resist delamination or peeling.

As shown in FIG. 3, there is both an adhesive bond (A) and a mechanical bond (B) between the coating material 30 and the apertured substrate 32. The mechanical bonds (B) occur when the coating material 30 is pulled within the apertures 38 and at least partially conforms to the sidewalls 39 of the apertures 38.

According to the present invention, the coating material can be applied in layers as thin as about 0.15 to about 0.25 mil. such that the composite material 44 does not have a "stiff" plastic feeling. Rather, the composite material is soft and has cloth-like tactile qualities. A further advantage is that a substantially thinner layer (and consequently, less amount) of coating material can be applied to the substrate. This decrease results in great cost savings. Further, low cost coating materials such as polyethylene films and other examples, including polyethylene and other polymeric materials can be applied to the substrate.

Still another advantage is that according to the method of the present invention, it is possible to dispense the coating material 30 onto the substrate 32 at a point close to the point of interface between the coating material 30 and the substrate 32. As seen in FIG. 2, it is possible to position the die 43 in a close adjacent relationship to the substrate 32. This close proximity between the coating material and the substrate 32 means that it is possible to apply the coated material at lower temperatures than were previously possible. Since the time lapse between when the coating material 32 leaves the die 43 and when the coating material 32 is dispensed onto the substrate 30 is less than in prior art methods, the total heat flux is less. For example, in the case of applying polyethylene, previous extrusion methods required that polyethylene be extruded at temperatures between about 550°–600° F. at a distance of about 1–3 feet above the substrate. When polyethylene is coated onto a substrate, according to the method of the present invention, the polyethylene is extruded at a temperature of about 500° F. at a preferred distance of about 2–5 inches from the substrate. It has been found that when temperatures are decreased even by about 10° F., there is better application of the coating material onto the substrate. Further, in certain embodiments, the vacuum also cools the substrate and the coating material quickly as the coating material is pulled into or against the top surface of the substrate.

Figure 4:
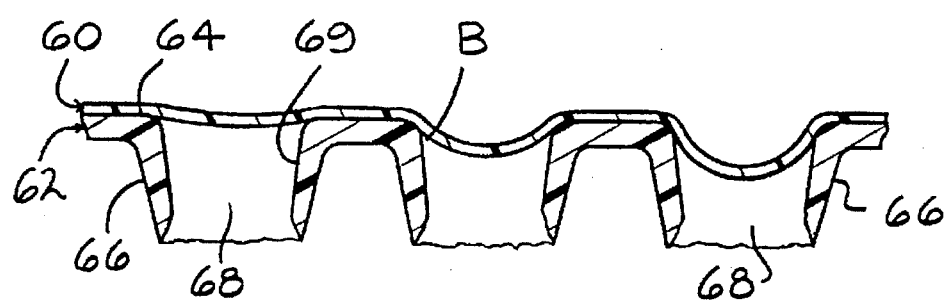
FIG. 4 is a simplified, greatly enlarged cross-sectional illustration of a coated three-dimensional substrate.

FIG. 4 shows one detailed embodiment of the present invention, wherein a coating material 60 is bonded to an apertured substrate 62. The apertured substrate has a planar or top surface 64 and a three-dimensional surface 66. A plurality of apertures 68 defined by sidewalls 69 extend from the three-dimensional surface 66. Mechanical bonds are formed at the areas "B", when the coating material 30 is applied adjacent sidewalls 69 of the apertures 68. The coating material 60 conforms somewhat to the interior diameters of the apertures 68, such that there is less stiffness or rigidity to the coating material 30.

Figure 5:
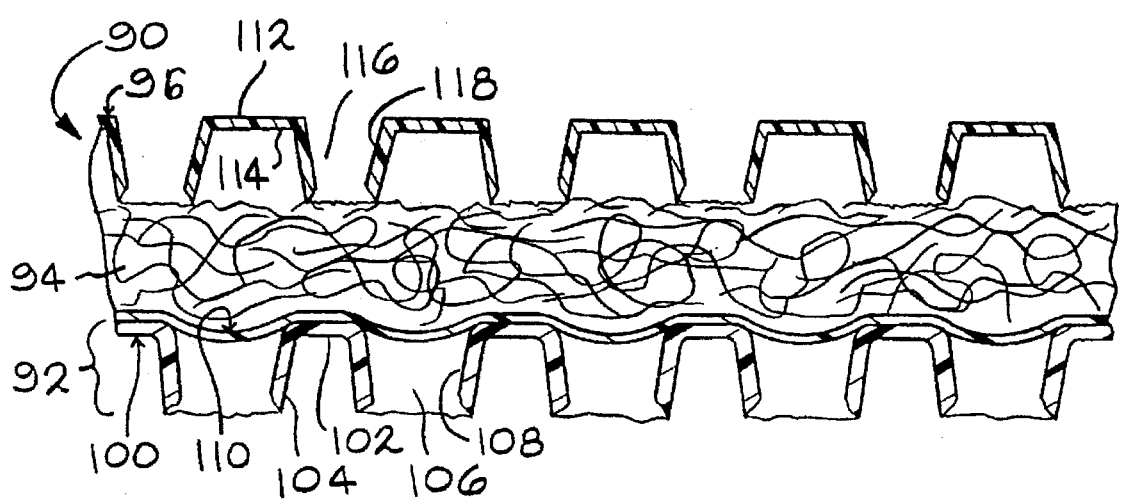
FIG. 5 is a simplified, greatly enlarged cross-sectional illustration of an extrusion coated microapertured substrate bonded to an absorbent pad and topsheet.

It is contemplated that various articles can be formulated using the film and method of the present invention. For example, FIG. 5 shows a section of a disposable product 90, generally comprising a coated substrate 92, an absorbent core 94, and a fluid pervious topsheet 96. The coated substrate 92 comprises a three-dimensional apertured substrate 100 having a planar surface 102 and a three-dimensional surface 104. The three-dimensional surface 104 defines a plurality of apertures 106 having sidewalls 108. A coating material 110 is adjacent the planar surface 102 of the apertured substrate 100. The absorbent core 94 is placed adjacent the coated substrate 110 and the fluid pervious topsheet 96 is adjacent the absorbent core 94. In the embodiment shown in FIG. 5, the fluid pervious topsheet 96 comprises a three-dimensional surface having a planar surface 112 and a three-dimensional surface 114 having a plurality of apertures 116, each of which are defined by sidewalls 118. It is contemplated that further layers such as a nonwoven layer (not shown) can be applied to the planar surface 112 of the fluid pervious topsheet 96.

Various other articles can be formulated using the method of the present invention. While particular embodiments of the present invention have been illustrated and described, it will be obvious to those skilled in the art that various changes and modifications can be made without parting from the spirit and scope of the invention and it is intended to cover in the claims herein all such modifications that are within the scope of this invention.

The invention claimed is:

1. A process for the manufacture of a liquid impervious multilayer composite material comprising a three-dimensional apertured substrate having a thin liquid impervious thermoplastic coating material thereon, the method of comprising:

(a) passing successive portions of the apertured substrate into contact with a continuous moving perforated member having a vacuum chamber which creates a pressure differential across the moving perforated member, the apertured substrate comprising a thermoplastic film material having a top planar surface and a bottom three-dimensional surface and a plurality of apertures extending therethrough, the apertures being defined by sidewalls having first open ends in the top planar surface and second open ends in the bottom, three-dimensional surface;

(b) subjecting the bottom surface of the apertured substrate to the pressure differential;

(c) supplying the liquid impervious thermoplastic coating material onto the top surface of the continuous moving apertured substrate, the liquid impervious coating material substantially covering the open ends of the apertures in the top surface of the apertured substrate, the pressure differential causing the liquid impervious thermoplastic coating material to adhere to the top surface of the apertured substrate material without substantially deforming the apertured substrate;

(d) maintaining the vacuum pressure differential for a period of time sufficient for the liquid impervious thermoplastic coating material to bond to the apertured substrate and form the liquid impervious multilayer composite material; and (e) removing the liquid impervious multilayer composite material from the moving member.

2. The method of claim 1, wherein as the pressure differential is applied to the bottom surface of the apertured substrate, portions of the liquid impervious thermoplastic coating material partially adhere to the sidewalls of each aperture.

3. The method of claim 1, wherein the liquid impervious thermoplastic coating material is extruded onto the apertured substrate at a temperature wherein the liquid impervious thermoplastic coating material adheres to the apertured substrate.

4. The method of claim 1, wherein the liquid impervious thermoplastic coating material is supplied from an extrusion member, the extrusion member being located about 2 to about 5 inches from the top surface of the apertured substrate.

5. The method of claim 4, wherein the extrusion member is about 2–3 inches from the top surface of the apertured substrate.

6. The method of claim 1, wherein the moving perforated member comprises a cylindrical drum.

7. The method of claim 1, wherein the moving perforated member comprises the outermost surface of an endless belt.

8. The method of claim 3, wherein the pressure differential cools the liquid impervious thermoplastic coating material as the fluid impervious thermoplastic coating material is applied to the apertured substrate.

9. The method of claim 1, wherein the liquid impervious thermoplastic coating material is applied at a thickness of about 0.15 to 0.25 mil.

10. A continuous method of forming a substantially fluid impervious composite material comprising a three-dimensional apertured substrate having a top surface and a bottom surface and a plurality of apertures extending therethrough, the apertured substrate having a fluid impervious coating material thereon, the method comprising the steps of:

(a) continuously bringing successive portions of the apertured substrate into contacting relation with a continuous moving member having a vacuum chamber which creates a pressure differential across the moving perforated member;

(b) applying the fluid impervious coating material in the direction of travel of the apertured substrate and substantially uniformly exposing the top surface of the apertured substrate to the fluid impervious coating material, the fluid impervious coating material having sufficient heat and mass flux to coat the apertured substrate, such that the fluid impervious coating material substantially conforms to at least the top surface of the apertured substrate;

(c) applying the pressure differential to the bottom surface of the apertured substrate as the fluid impervious coating material is applied thereto to form the substantially fluid impervious composite material, the pressure differential being sufficient to cause the fluid impervious coating material to bond to the top surface of the apertured substrate without causing any perforations in the fluid impervious coating material and without substantially deforming the apertured substrate; and (d) removing the substantially fluid impervious composite material from the moving member.

\* \* \* \* \*